(12) United States Patent
Bertling

(10) Patent No.: US 6,479,644 B1
(45) Date of Patent: Nov. 12, 2002

(54) METHOD FOR PURIFYING AND ENRICHING MOLECULES

(76) Inventor: Wolf Bertling, Meisenweg 22, 91056 Erlangen (DE)

( * ) Notice: Subject to any disclaimer, the term of this patent is extended or adjusted under 35 U.S.C. 154(b) by 0 days.

(21) Appl. No.: 09/214,629

(22) PCT Filed: Jun. 28, 1997

(86) PCT No.: PCT/DE97/01368

§ 371 Date: Jan. 8, 1999

§ 102(e) Date: Jan. 8, 1999

(87) PCT Pub. No.: WO98/02399

PCT Pub. Date: Jan. 22, 1998

(30) Foreign Application Priority Data

Jul. 12, 1996 (DE) .......................................... 196 28 171
Feb. 10, 1997 (DE) ...................................... 297 02 254 U

(51) Int. Cl.$^7$ .......................... C07K 17/00; C12Q 1/68; C12M 1/36; C25C 1/22; C25D 5/00
(52) U.S. Cl. .......................... 530/412; 435/6; 435/91.2; 435/283.1; 435/287.2; 435/291.5; 205/43; 205/50; 205/81; 422/68.1; 530/412
(58) Field of Search .................. 435/6, 91.2, 283.1, 435/287.2, 291.5; 205/43, 50, 81; 422/68.1; 530/412

(56) References Cited

U.S. PATENT DOCUMENTS

| 4,545,888 | A | | 10/1985 | Walsh |
|---|---|---|---|---|
| 4,715,942 | A | | 12/1987 | Tezuka et al. |
| 4,915,811 | A | | 4/1990 | Yamamoto et al. |
| 4,966,675 | A | * | 10/1990 | Steininger et al. .......... 204/290 |
| 5,151,165 | A | | 9/1992 | Huynh |
| 5,196,099 | A | | 3/1993 | Mori et al. |
| 5,217,593 | A | | 6/1993 | MacConnell |
| 5,434,049 | A | * | 7/1995 | Okano et al. |
| 5,776,672 | A | * | 7/1998 | Hashimoto et al. ............ 435/6 |
| 5,871,918 | A | * | 2/1999 | Thorp et al. |
| 5,968,745 | A | * | 10/1999 | Thorp et al. |
| 6,017,696 | A | * | 1/2000 | Heller et al. .................. 422/50 |

FOREIGN PATENT DOCUMENTS

| EP | 0 031 565 A2 | | 12/1980 |
|---|---|---|---|
| FR | 2 687 931 A1 | | 2/1992 |
| GB | WO 89/05454 | | 6/1989 |
| WO | WO89/10556 | * | 11/1989 |
| WO | WO 94/25144 | | 10/1994 |

* cited by examiner

Primary Examiner—Jeffrey Siew
(74) Attorney, Agent, or Firm—Pearne & Gordon LLP

(57) ABSTRACT

The invention relates to a process for purifying and concentrating charge-bearing first molecules 9, such as proteins, nucleic acids and the like, comprising the following steps:

a) preparation of a solution containing the first molecules 9, b) contacting the solution with an electrode 2 which is directly provided with a coating of second molecules 4 having affinity for the first molecules 9, and c) connecting the electrode 2 to a means 11 for generating an electric field to bring about a movement of the first molecules 9 in the solution directed relative to the electrode 2.

33 Claims, 4 Drawing Sheets

METHOD FOR PURIFYING AND ENRICHING MOLECULES

BACKGROUND OF THE INVENTION

The invention relates to a process and an apparatus for purifying and concentrating charge-bearing first molecules such as proteins, nucleic acids and the like.

Molecules of biological relevance, such as nucleic acids, can be concentrated for carrying out analytical tests, for example the polymerase chain reaction (PCR), by precipitating the nucleic acids, by binding the nucleic acids to a suitable matrix, for example using an ion exchange column, and by various centrifugation methods. Specific nucleic acids can be selected from a nucleic acid mixture by concentrating and separating in a gel, by hybridizing to membranes or by complexing with specific proteins. Similar processes are used to purify proteins; also used in this instance are processes like high pressure liquid chromatography (HPLC) and antibody-dependent purification processes. Antibody-dependent processes use molecules immobilized on surfaces, such as, for example, latex beads. Known processes have the disadvantage of inadequate sensitivity and speed. In addition, they are costly to carry out.

The present invention is based on the object of providing a purification and concentration process and a corresponding apparatus with which the disadvantages of the prior art are eliminated. It is additionally intended to be possible to concentrate in particular nucleic acids, proteins and other charge-bearing molecules of predetermined degree of homology or predetermined binding affinity from a large volume.

SUMMARY OF THE INVENTION

According to the process of the invention, the object is achieved by the following steps:
  a) preparation of a solution containing the first molecules,
  b) contacting the solution with at least one electrode which is directly provided with a coating of second molecules having affinity for the first molecules, and
  c) connecting the electrode to a means for generating an electric field to bring about a movement of the first molecules in the solution directed relative to the coating.

The electrode is expediently produced from an electrically conducting plastic. It can be a layer on an electrically nonconducting plastic support rod or a section, preferably terminal, of such a plastic support rod. It is also possible for the plastic support rod to be produced completely from electrically conducting plastic and to be provided with a handle element which is produced from an electrically nonconducting plastic and can be, for example, slipped on.

On exposure to the electric field there is utilization of the effect that the first molecules present in solution, for example nucleic acid molecules, are charge-bearing and thus able to move in the electric field. The second molecules, which due to exposure to the electric field have come into contact with or reach the direct vicinity of the coating, can bind to the first molecules thereon. Suitable binding in this case may be, in particular, ionic, covalent, hydrogen bonding or binding brought about by steric effects. No electric field may be applied while this binding is developing. The process according to the invention can be used not only when the first molecules are present in a solution. It is sufficient for the first molecules to be present in a matrix, for example gel, meat or the like, which permits migration thereof in the electric field.

BRIEF DESCRIPTION OF THE SEVERAL VIEWS OF THE DRAWING

Examples of the embodiments of the invention are explained by means of the drawing below wherein.

DETAILED DESCRIPTION OF THE PREFERRED EMBODIMENTS

Figure 1:
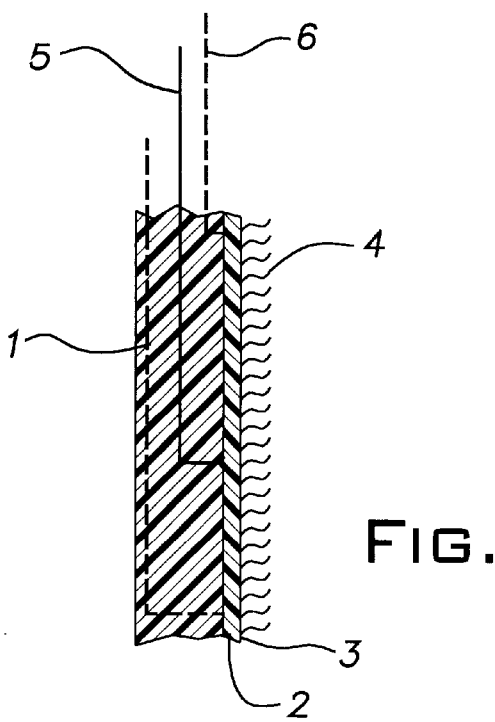
FIG. 1 is a diagrammatic cross-section through a first example of an electrode embodiment.

In one embodiment of the invention, the electric field is generated by applying a first voltage to the electrode so that it acts as anode to which first molecules bearing a negative charge, for example nucleic acid molecules, are attracted so that binding to the second molecules is achieved. In an alternative embodiment, the electric field is generated by applying a first voltage to the electrode so that it acts as cathode to which first molecules bearing a positive charge, for example proteins, are attracted so that binding to the second molecules is achieved.

It is regarded as particularly advantageous for the following step to be carried out in particular after the binding of the first to the second molecules:

$d_1$) reversing the polarity and applying a second voltage so that the electrode acts as cathode from which first molecules bearing a negative charge, for example nucleic acids, are repelled.

As an alternative to this, the following step can be carried out in particular after the binding of the first to the second molecules:

$d_2$) reversing the polarity and applying a second voltage so that the electrode acts as anode from which first molecules bearing a positive charge, for example proteins, are repelled.

Blockage of the coating can be prevented by steps $d_1$) and $d_2$). This is because it is possible, by suitable choice of the second voltage, to repel charge-bearing species which are not bound to the coating from the coating and thus improve access for further first molecules. It is additionally possible, by suitably increasing the second voltage, for particular charge-bearing first molecules to be specifically removed from the coating. It is also possible in this way to achieve selection of particular first molecules. This phenomenon is known as stringency of a hybridization reaction for nucleic acids.

Care must be taken in the reversal of polarity that the migration of those first molecules which have entered into interaction with the second molecules or hybridize with the latter is limited. The extent of this hindrance depends on the nature and number of the interactions, that is primarily on the degree of homology of the first and second molecules interacting with one another, or their affinity. First molecules which have high affinity or complementarity with the second molecules are held back most strongly in this case.

It is expedient to carry out the following step during and/or after step c:

e) heating the electrode or the solution so that the first molecules are thermally dissociated or denatured into their components or subunits, for example single-stranded nucleic acids.

This embodiment makes it possible, for example, to melt double-stranded nucleic acids attracted to the coating and thus facilitates the binding of the single strands to, for example, complementary oligonucleotides provided in the coating. Keeping the surface at a particular temperature thus also makes a contribution to the stringency of the selection of particular first binding molecules.

It is expedient to carry out the following step in particular after step $d_1$ or $d_2$:

f) cooling the electrode or the solution to bring about binding of the first molecules, components and/or subunits thereof to the second molecules.

Step f additionally assists the binding of the first molecules, their components or subunits to the coating.

It is possible, depending on the nature of the first molecules, to repeat one or more of steps c–e.

It is expedient, especially during and/or after step $d_1$ or $d_2$, to mix the solution, preferably mechanically. Removal of first molecules, components and/or subunits repelled from the electrode by steps $d_1$ and $d_2$, is assisted in this way.

The maximum values of the first and second voltage are advantageously chosen so that degradation of the first and second molecules, and the components and/or subunits, by electrolysis is avoided. It has additionally proven beneficial to choose the maximum value of the second voltage so that breaking of linkages formed between the first molecules or their components or subunits and the second molecules is avoided.

It is possible, by adapting to the nature of the first molecule to be concentrated or purified, to control, preferably automatically, the maximum values of the first and/or second voltage(s), the duration of the polarity and reverse polarity and/or the temperature of the electrode as a function of parameters of the solution such as its pH, ionic conductivity, concentration of first molecules, temperature and the like.

According to the achievement in terms of apparatus, an apparatus for concentrating charge-bearing first molecules present in a solution, such as nucleic acids, proteins and the like, is provided with an electrode which is directly provided with a coating of second molecules having affinity for the first molecules, and where the electrode is connected to a means for generating an electric field so that it is possible to bring about a movement of the first molecules in the solution directed relative to the electrode.

This means that an apparatus for carrying out the process according to the innovation is made available with which the disadvantageous blocking of the coating is avoided and it is possible to bring about concentration of specific molecules on a surface. The electrode can be produced simply and cheaply; it can therefore be used as disposable article.

The electrode is preferably produced from an electrically conducting plastic, in particular a polycarbonate, a polycarbene, polycarbonate copolymer or homopolymer with a conducting additive such as graphite. Electrically conducting plastics of this type are disclosed, for example in DE 35 41 721 A1, the contents of which are incorporated herein by reference.

The means for generating the electric field can be a means for generating an alternating electric field. It is thus possible to achieve rapid and specific occupation of the coating with the first molecules to be concentrated or purified.

Depending on whether the first molecule has a positive or negative charge, the means for generating the electric field may comprise the electrode as anode or as cathode.

The plastics present as electrode material permit the chemistry of coating (Hitoshi Kohsaka: J. Clin. Lab. Anal. 8:452–455 (1994)) with the second molecules predetermining the selection criteria to be very simple and thus low-cost. The coating provided on the electrode has, according to another embodiment feature, at least one aliphatic radical which is preferably linked to the electrode via an NH or SH linkage. The aliphatic radical may in this case have a chain length of 2–20, preferably of 6–10, carbon atoms. A protein sequence, peptide sequence or nucleotide sequence is expediently linked to the free end of the aliphatic radical. The nucleotide sequence may comprise 5–30 nucleotides. It is moreover advantageous for the nucleotide sequence to be a first oligonucleotide formed by a chain of 10–20, preferably 15, nucleotides. It is regarded as particularly advantageous to link a second oligonucleotide, preferably via a sugar-phosphate linkage, to the first oligonucleotide.

The electrode can be provided with a heating element which is separated from the electrode by an electrical insulator. The insulator can be produced from glass or ceramic, preferably from aluminum oxide or nitride. The heating element can be a resistance heating element produced from platinum. The resistance heating element can, in one embodiment of the invention, also be identical to the electrode because, with suitable circuitry, the high electrical resistance, by comparison with the leads, of the plastic electrode can be used to heat the electrode surface.

In order to divert unwanted molecules away from the coating and bring about redistribution of first molecules to be purified and concentrated in the solution, it is expedient to provide a means for mixing the solution. This may be a stirrer which can be operated electrically or a stream of gas passed through.

According to another embodiment feature of the invention, the electrical quantities for generating the electric field and for operating the heating element and the means for mixing can be controlled, preferably automatically, as a function of parameters of the solution such as its pH, ionic conductivity, concentration of first molecules, temperature and the like. A computer will expediently be used for automatic control.

Finally, a combination of means for producing the apparatus according to the innovation and for carrying out the process according to the innovation are claimed.

EXAMPLE 1

Construction of the Coating and of the Element Located Underneath

A first insulating layer which can be formed from glass or ceramic, for example from aluminum oxide, is applied to a support rod. To this is applied a conducting layer, for example produced in the form of a platinum zigzag, for heating. The conducting layer is in turn covered by a thin second insulating layer. It may have a thickness of 150 µm and be produced from glass. On this is located an electrode formed from gold. It is bonded.

The coating is provided on the electrode. C6 aliphatic linker molecules are linked via SH groups to the surface of the electrode. Spacer molecules, for example oligonucleotides consisting of 10 thymidine residues, are in each case linked to the free end of the linker molecules. 10 pmol of a 20-mer with a predetermined sequence is linked in each case to their free ends via a sugar-phosphate linkage. The electrode provided with the coating is normally used in combination with the claimed apparatus. However, it may also relate to a separate innovation.

EXAMPLE 2

Purification

The electrode described in Example 1 is immersed in 1 ml of a measurement solution containing 20 pmol of radiolabeled oligonucleotide (20-mer) and 40 pmol of DNA single strands. The oligonucleotide is complementary to the oligonucleotide bound in the coating, whereas the DNA single strands are not. The following results are obtained for the activity of the coating determined by means of Cherenkov counting:

Application of a voltage of 0.2 V and a current of 0.8 mA to the electrode results, after reversal of the polarity several times, in a binding of 9% of the total activity to the coating. On-connection of the electrode as anode for two minutes without reversal of polarity there is 2% binding of the total activity. Without application of a voltage, less than 0.2% of the total activity is bound to the coating.

A support rod 1 produced from Teflon is provided with a conducting layer or electrode 2 consisting of an electrically conducting plastic. The surface 3, facing the solution (not depicted here), of the electrode 2 is coated with oligonucleotides 4. A first lead 5 is embedded in the support rod 1 and is bonded to the electrode 2. Two other second leads 6 (depicted here by a broken line) can likewise be bonded to the electrode 2 for heating.

Figure 2:
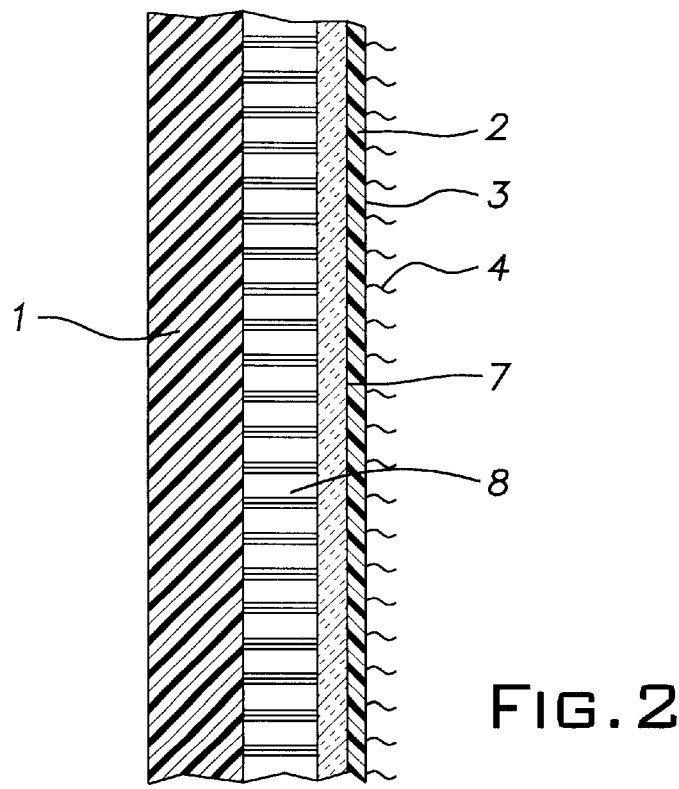
FIG. 2 is a diagrammatic cross-section through a second example of an electrode embodiment.

In the example of an embodiment shown in FIG. 2, an electrically insulating intermediate layer 7 is additionally provided between the electrode 2 and the support rod 1. It separates the electrode 2 from a heating layer 8 which is provided directly on the support rod 1 produced from Teflon.

Figure 3:
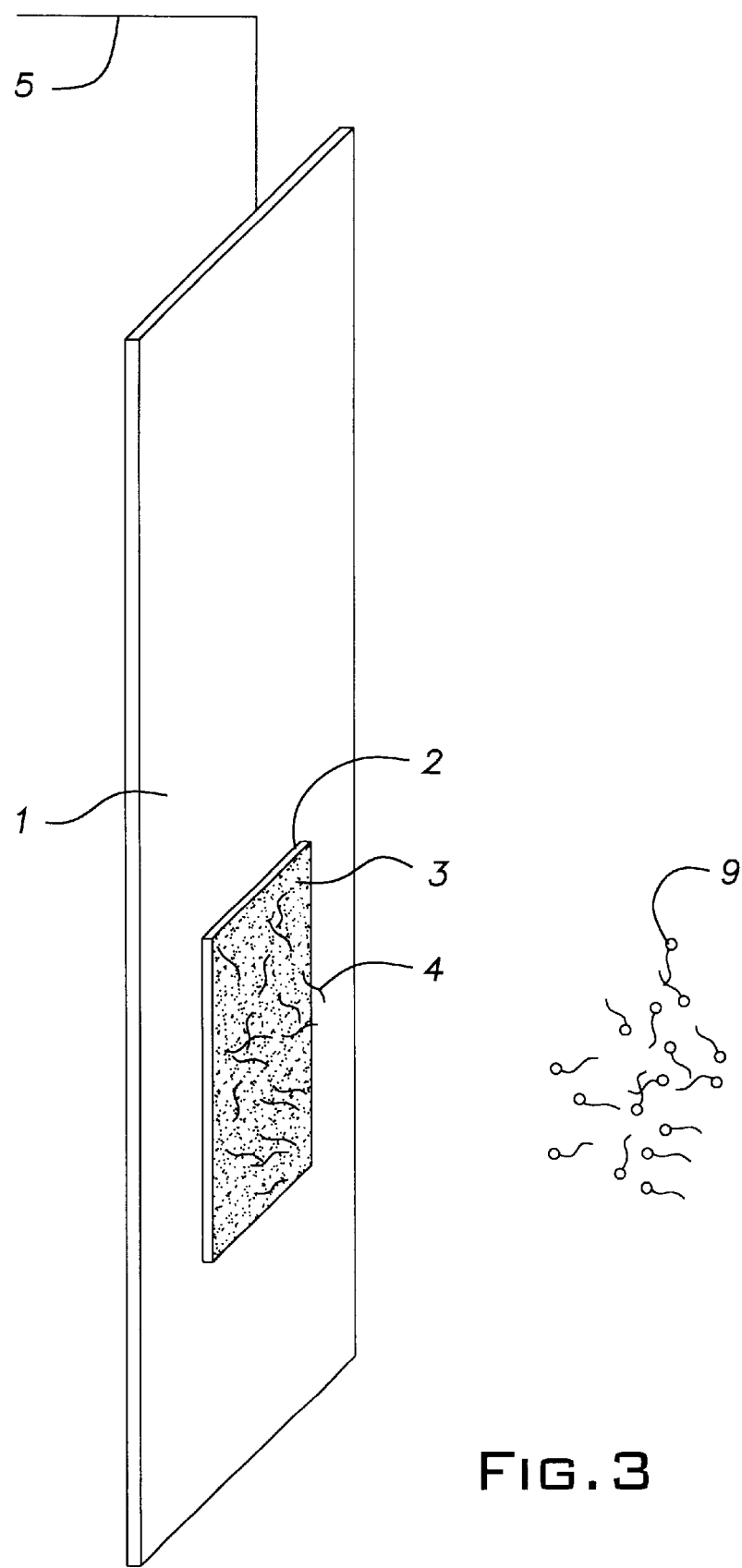
FIG. 3 is a perspective view according to FIG. 1.

FIG. 3 shows a perspective view of the example of an embodiment described in FIG. 1. 9 designates chargebearing first molecules present in a solution.

Figure 4:
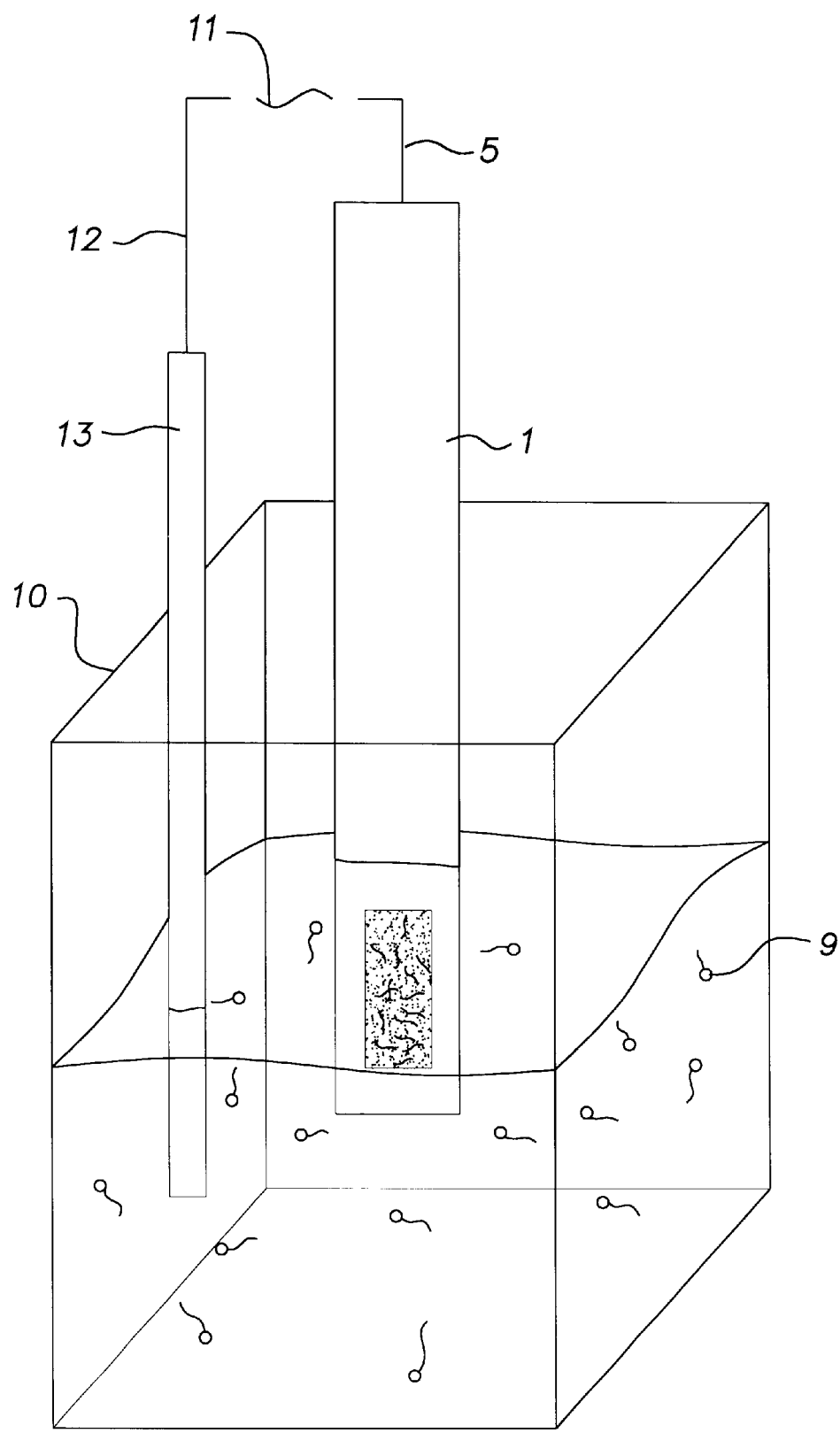
FIG. 4 is a perspective view of a container with an electrode and a counter electrode.

FIG. 4 shows the example of an embodiment according to FIG. 3 in perspective view. The support rod 1 is immersed in a solution which is accommodated in a container 10 and in which first molecules 9 are present. The first lead 5 is connected to a source of alternating voltage 11. Likewise connected to the source of alternating voltage 11 is, via a third lead 12, a counter electrode 13 immersed in the solution.

Figure 5:
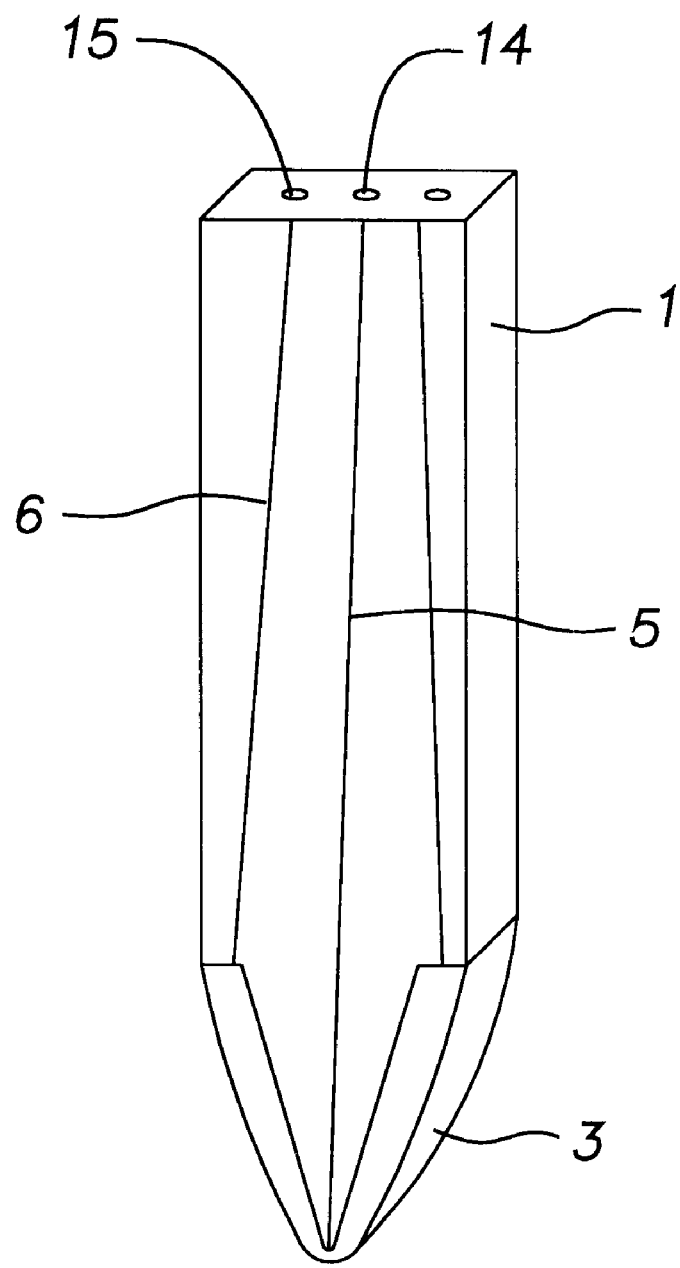
FIG. 5 is a perspective view of a third example of an electrode embodiment.

FIG. 5 shows a perspective view of a third example of an electrode embodiment. The surface 3 of electrode 2 is present at the tip of the support rod 1 produced from insulating plastic. The embedded first lead 5 is connected to a first connecting socket 14 and the second leads 6 are each connected to second connecting sockets 15. Plugs of connecting cables can be inserted into connecting sockets 14 and 15.

The apparatus functions in the following way:

In order to isolate biomolecule samples from a solution, an apparatus according to the invention is immersed in the solution. Then a voltage is applied through the electrode 2 provided on the support rod 1 and through a counter electrode 13 immersed in the solution. Depending on the polarization of electrode 2, this brings about electrophoretic migration of oppositely charged biomolecules in the direction of electrode 2. When the coating consisting of oligonucleotides 4 is reached, the latter are bound thereto.

In the case of double-stranded DNA, the polarization of electrode 2 is interrupted after a predetermined time. Heating of electrode 2 then takes place. This breaks down the DNA double strands adhering to oligonucleotides 4 into their components. Reapplication of the polarization moves the single strands back to the oligonucleotides 4, where they are bound. Samples can be obtained simply and rapidly from the solution in this way.

List of Reference Numbers

1 Support rod
2 Electrode
3 Surface
4 oligonucleotides
5 First lead
6 Second lead
7 Intermediate layer
8 Heating layer
9 First molecules
10 Container
11 Source of alternating voltage
12 Third lead
13 Counter electrode
14 First connecting socket
15 Second connecting socket

What is claimed is:

1. A process for concentrating chargebearing first molecules from a crude solution, comprising the following steps:
   a) preparing a crude solution containing the first molecules,
   b) contacting the solution with an electrode which is directly provided with a coating of second molecules having affinity for the first molecules, said electrode consisting of conducting plastic,
   c) connecting the electrode to a means for generating an electric field,
   d) generating an electric field effective to direct the movement of the first molecules relative to the electrode,
   e) binding a portion of the first molecules to a portion of the second molecules,
   f) reversing the polarity of the electrode to repel chargebearing species that are not bound to the second molecules to improve access for further first molecules, and
   g) concentrating said first molecules by way of steps a) through f).

2. The process as claimed in claim 1, wherein to generate the electric field a first voltage is applied to the electrode so that it acts as an anode to which the first molecules bearing a negative charge are attracted so that binding to the second molecules is achieved.

3. The process as claimed in claim 2, wherein the following step is carried out after the binding of the first molecules to the second molecules:
   after the step of generating the electric field, reversing polarity of the field and applying a second voltage so that the electrode acts as a cathode from which first molecules bearing a negative charge are repelled.

4. The process as claimed in claim 3, wherein the following step is carried out during step c:
   heating the electrode or the solution so that the first molecules are thermally dissociated or denatured into their components or subunits.

5. The process as claimed in claim 4, wherein the following step is carried out after the step of reversing the polarity:

cooling the electrode or the solution to bring about binding at least one of the first molecules, components or subunits to the second molecules.

6. The process as claimed in claim 5, wherein one or more of the recited steps are repeated.

7. The process as claimed in claim 6, wherein the solution is mixed.

8. The process as claimed in claim 3, wherein maximum values of the first and second voltages are chosen so that degradation or dissociation of the first and second molecules, and the components and subunits, by electrolysis is avoided.

9. The process as claimed in claim 3, wherein a maximum value of the second voltage is chosen so that breaking of linkages formed between at least one of the first molecules, their components, or their subunits, and the second molecules is avoided.

10. The process as claimed in claim 3, wherein a maximum value of at least one of the first voltage, the second voltage, the duration of the polarity and reverse polarity or the temperature of the electrode are controlled as a function of at least one physical parameter of the solution.

11. The process as claimed in claim 1, wherein to generate the electric field a first voltage is applied to the electrode so that it acts as a cathode to which the first molecules bearing a positive charge are attracted, so that binding of the first molecules to the second molecules is achieved.

12. The process as claimed in claim 11, wherein the following step is carried out after the binding of the first molecules to the second molecules:

reversing the polarity of the field and applying a second voltage so that the electrode acts as an anode from which first molecules bearing a positive charge are repelled.

13. The process as claimed in claim 12, wherein the following step is carried out during step c:

heating at least one of the electrode and the solution, so that the first molecules are thermally dissociated or denatured into their components or subunits.

14. The process as claimed in claim 13, wherein the following step is carried out after the step of reversing the polarity of the electric field:

cooling at least one of the electrode and the solution to bring about binding at least one of the first molecules, components or subunits to the second molecules.

15. The process as claimed in claim 14, wherein one or more of the recited steps are repeated.

16. The process as claimed in claim 15, wherein the solution is mixed.

17. The process as claimed in claim 16, wherein maximum values of the first and second voltage are chosen so that degradation or dissociation of the first and second molecules, and the components and subunits, by electrolysis is avoided.

18. The process as claimed in claim 17, wherein maximum value of the second voltage is chosen so that breaking of linkages formed between the first molecules or their components or subunits and the second molecules is avoided.

19. The process as claimed in claim 18, wherein a maximum value of at least one of the first voltage, the second voltage, the duration of the polarity and reverse polarity or the temperature of the electrode are controlled as a function of at least one physical parameter of the solution.

20. The process as claimed in claim 3, wherein the first molecules are nucleic acids.

21. The process as claimed in claim 3, wherein the following step is carried out after step c:

heating the electrode or the solution so that the first molecules are thermally dissociated or denatured into their components or subunits.

22. The process as claimed in claim 4, wherein said components comprise single-stranded nucleic acids.

23. The process as claimed in claim 21, wherein said components comprise single-stranded nucleic acids.

24. The process as claimed in claim 7, wherein the solution is mechanically mixed.

25. The process as claimed in claim 10, wherein the physical parameter is selected from the group consisting of pH, ionic conductivity, concentration of first molecules and temperature.

26. The process as claimed in claim 11, wherein the first molecules comprise proteins.

27. The process as claimed in claim 12, wherein the first molecules comprise proteins.

28. The process as claimed in claim 12, wherein the following step is carried out after step c:

heating the electrode or the solution so that the first molecules are thermally dissociated or denatured into their components or subunits.

29. The process as claimed in claim 13, wherein said components comprise single-stranded nucleic acids.

30. The process as claimed in claim 28, wherein said components comprise single-stranded nucleic acids.

31. The process as claimed in claim 16, wherein the solution is mechanically mixed.

32. The process as claimed in claim 19, wherein the physical parameter is selected from the group consisting of pH, ionic conductivity, concentration of first molecules and temperature.

33. The process as claimed in claim 2 wherein the first molecules are nucleic acids.

* * * * *

UNITED STATES PATENT AND TRADEMARK OFFICE
CERTIFICATE OF CORRECTION

PATENT NO. : 6,479,644 B1
DATED : November 12, 2002
INVENTOR(S) : Wolf Bertling

It is certified that error appears in the above-identified patent and that said Letters Patent is hereby corrected as shown below:

Title page,
Item [86], "§ 371 Date", please delete "Jan. 8, 1999", and insert therefor
-- March 8, 1999 --; and
"§ 102(e) Date", please delete "Jan. 8, 1999", and insert therefor -- March 8, 1999 --.

Column 1,
Line 4, please delete "BACKGROUND OF THE INVENTION".
Line 8, before the paragraph beginning "Molecules of biological relevance…", on a new line, please insert therefor -- BACKGROUND OF THE INVENTION --.

Column 5,
Line 19, please delete "On-connection", and insert therefor -- On connection --.

Signed and Sealed this

Seventeenth Day of June, 2003

JAMES E. ROGAN
*Director of the United States Patent and Trademark Office*